United States Patent
Coe et al.

[11] Patent Number: 5,961,505
[45] Date of Patent: Oct. 5, 1999

[54] ABSORBENT ARTICLE EXHIBITING IMPROVED FLUID MANAGEMENT

[75] Inventors: Louise Cynthia Ellis Coe, Appleton; Laura Jane Anderson, Menasha; Mark Leonard Kaspar, Oshkosh; Mary Lou McDaniel, Appleton, all of Wis.; John Carl Faison, Cumming, Ga.; Andrew Edward Diamond, Roswell, Ga.; Mary Chris Wanek; David Keith Osteen, both of Marietta, Ga.; Kenneth Yin Wang, Westchester, Pa.

[73] Assignee: Kimberly-Clark-Worldwide, Inc., Neenah, Wis.

[21] Appl. No.: 08/200,251

[22] Filed: Feb. 23, 1994

Related U.S. Application Data

[63] Continuation of application No. 07/980,137, Nov. 23, 1992, abandoned, which is a continuation of application No. 07/731,589, Jul. 17, 1991, abandoned.

[51] Int. Cl.$^6$ ............................. A61F 13/15; A61F 13/20
[52] U.S. Cl. ...................... 604/378; 604/358; 604/385.1; 604/383
[58] Field of Search .................................. 604/378, 383, 604/385.1, 358

[56] References Cited

U.S. PATENT DOCUMENTS

| | | |
|---|---|---|
| 2,295,439 | 9/1942 | Voigtman . |
| 2,564,689 | 8/1951 | Harwood et al. . |
| 2,900,980 | 8/1959 | Harwood . |
| 3,676,242 | 7/1972 | Prentice ............................. 156/62.4 |
| 3,888,254 | 6/1975 | Hendricks . |
| 3,929,135 | 12/1975 | Thompson . |
| 3,945,386 | 3/1976 | Anczurowski et al. . |
| 3,965,906 | 6/1976 | Karami . |
| 3,967,623 | 7/1976 | Butterworth et al. . |
| 3,994,299 | 11/1976 | Karami . |
| 4,014,341 | 3/1977 | Karami . |
| 4,285,342 | 8/1981 | Mesek . |
| 4,323,068 | 4/1982 | Aziz . |
| 4,323,069 | 4/1982 | Ahr et al. . |
| 4,324,246 | 4/1982 | Mullane et al. . |
| 4,333,465 | 6/1982 | Wiegner . |
| 4,340,563 | 7/1982 | Appel et al. ............................. 264/518 |
| 4,381,782 | 5/1983 | Mazurak et al. ........................ 604/368 |
| 4,397,644 | 8/1983 | Matthews et al. ....................... 604/378 |
| 4,480,000 | 10/1984 | Watanabe et al. ....................... 428/284 |

(List continued on next page.)

FOREIGN PATENT DOCUMENTS

| | | |
|---|---|---|
| 0088738A1 | 9/1983 | European Pat. Off. . |
| 0272683A2 | 6/1988 | European Pat. Off. . |
| 0321985A2 | 6/1989 | European Pat. Off. . |
| 0329160A2 | 8/1989 | European Pat. Off. . |
| 1122727 | 8/1989 | Japan . |
| 2096002 | 10/1982 | United Kingdom . |
| 2124907 | 2/1984 | United Kingdom . |
| 2180162 | 3/1987 | United Kingdom . |

*Primary Examiner*—Mickey Yu
*Assistant Examiner*—Tram A. Nguyen
*Attorney, Agent, or Firm*—Thomas M. Parker

[57] ABSTRACT

An absorbent article is disclosed which exhibits improved fluid management. The article includes an absorbent having first and second oppositely aligned surfaces and a longitudinally extending central axis. A bicomponent cover is positioned over the first surface of the absorbent and includes a first and a second material. The first material has openings formed therein and is aligned along the longitudinally extending central axis of the absorbent. The second material is nonapertured and is secured to, or positioned adjacent to, the outer periphery of the first material. The first and second materials cooperate to enclose the absorbent. Positioned between the first material and the first surface of the absorbent is a separation means. The separation means directs fluid from the body downward, in the z direction, away from the bicomponent cover, and outward in the x and y directions to provide a more efficient use of the absorbent material. The absorbent article further contains a liquid-impermeable baffle which is positioned adjacent to the second surface of the absorbent.

48 Claims, 4 Drawing Sheets

U.S. PATENT DOCUMENTS

| | | | |
|---|---|---|---|
| 4,519,799 | 5/1985 | Sakurai et al. | 604/366 |
| 4,636,209 | 1/1987 | Lassen | 604/378 |
| 4,675,013 | 6/1987 | Ruffo | 604/366 |
| 4,676,786 | 6/1987 | Nishino | 604/378 |
| 4,690,679 | 9/1987 | Mattingly, III et al. | 604/383 |
| 4,710,186 | 12/1987 | DeRossett et al. | 604/383 |
| 4,725,473 | 2/1988 | Van Gompel et al. | 428/156 |
| 4,741,941 | 5/1988 | Englebert et al. | 428/71 |
| 4,755,413 | 7/1988 | Morris | 428/138 |
| 4,762,520 | 8/1988 | Wallstrom | 604/366 |
| 4,798,603 | 1/1989 | Meyer et al. | 604/378 |
| 4,798,604 | 1/1989 | Carter | 604/383 |
| 4,806,411 | 2/1989 | Mattingly, III et al. | 428/139 |
| 4,878,974 | 11/1989 | Kagawa | 156/85 |
| 4,908,026 | 3/1990 | Sukiennik et al. | 604/378 |

ABSORBENT ARTICLE EXHIBITING IMPROVED FLUID MANAGEMENT

CROSS REFERENCE TO RELATED APPLICATIONS

This is a continuation application of copending U.S. application Ser. No. 07/980,137, now abandoned, filed on Nov. 23, 1992, which is a File Wrapper Continuation of abandoned U.S. application Ser. No. 07/731,589, filed on Jul. 17, 1991.

FIELD OF THE INVENTION

This invention relates to an absorbent article which exhibits improved fluid management. More particularly, this invention relates to an absorbent article having a bicomponent cover and a separation means positioned therebelow. The separation means directs the body fluid downward, in the z direction, away from the bicomponent cover and into the absorbent.

BACKGROUND OF THE INVENTION

Disposable absorbent articles, such as sanitary napkins, catamenial pads, pantiliners, diapers, training pants, incontinent garments, and the like, are designed to be worn adjacent to a human body to absorb discharged body fluids. The body fluids can include urine, blood, menses and other excrements discharged by the body at various times, such as during a bowel movement or during a menstrual period. Such articles are normally multilayered in construction and include a liquid-permeable cover, a liquid-impermeable baffle and a hydrophilic absorbent core positioned therebetween. The article can also include a transfer and/or distribution layer situated between the cover and the absorbent core which directs body fluid downward, away from the cover, and distributes the fluid in the x and y directions. The cover is designed to allow rapid transfer of body fluid down into the absorbent core, where it can be retained. The baffle serves to prevent fluid present in the absorbent core from leaking out of, and soiling or staining, an undergarment or another adjacent piece of clothing.

Numerous prior art patents exist which teach different materials and constructions for the cover layer. The initial use of nonwoven materials has evolved into the use of one or more nonwoven fibrous layers, along with a film layer containing apertures. U.S. Pat. Nos. 3,945,386; 3,965,906; 3,967,623; 3,994,299; 4,014,341; 4,323,069 and 4,324,246 teach such combinations. Other patents, such as U.S. Pat. Nos. 3,888,254 and 4,675,013, teach the use of a cover layer which is laminated to other fibrous sheets. U.S. Pat. No. 4,762,520 teaches forming a cover from a carded fiber fabric containing melt fibers sub-divided into parallel streaks. Other U.S. patents, such as U.S. Pat. Nos. 4,710,186; 4,755,413; 4,798,604 and 4,806,411, teach forming apertures in the cover. U.S. Pat. No. 4,333,465 teaches a cover comprised of a liquid-impermeable composite material having a liquid-permeable zone. Lastly, U.S. Pat. Nos. 3,676,242; 4,690,679; 4,725,473 and 4,878,974 teach various methods of making film and fiber composite cover materials by coextrusion, laminating, and the like.

Two patent applications filed by Kimberly-Clark Corporation, which relate to nonwoven webs, include U.S. Ser. No. 07/608,095, filed Nov. 1, 1990, by inventors H. K. Barnes et al., entitled "HYDRAULICALLY NEEDLED NONWOVEN PULP FIBER WEB", now U.S. Pat. No. 5,137,600, and U.S. Ser. No. 07/633,594, filed Dec. 21, 1990, by inventors C. Everhart et al., entitled "HIGH PULP CONTENT NONWOVEN COMPOSITE FABRIC", now abandoned.

Presently, some manufacturers are moving toward the use of two or more different kinds of materials for the cover in order to enhance the functionality of the cover layer. Published Japanese patent application 122,727 (1989) teaches a sanitary napkin which has a cover constructed of two different hydrophobic materials, both of which contain apertures. U.S. Pat. No. 4,285,342 issued to Mesek is somewhat similar except, instead of using two different kinds of materials, a large opening is formed in the cover layer of a diaper to enhance fluid flow into the absorbent core. U.K. patent 2,124,907 issued to Lloyd teaches a fabric bonded to a water-impermeable material, with both materials located on the bodyside surface of the absorbent device.

In order for an absorbent article to exhibit improved fluid management, it should utilize one or more layers located between the cover and the absorbent. Such layer(s) should assist in keeping the cover dry by directing body fluid downward, in the z direction, away from the cover. The layer(s) can also function to move the body fluid outward, in the x and y directions, so as to facilitate rapid fluid intake by the absorbent. U.S. Pat. No. 4,908,026 issued to Sukiennik et al. teaches the use of a flow zone control layer located beneath the cover for facilitating dispersion of body fluid along the length of the absorbent article, before allowing the fluid to pass into the absorbent. Other U.S. patents, which teach the use of a fluid transfer or a fluid distribution layer beneath the cover, include U.S. Pat. Nos. 4,397,644; 4,480,000; 4,519,799 and 4,798,603. These patents teach various materials and compositions for the transfer or distribution layer, which assist in directing the body fluid downward, into the absorbent.

Now, an absorbent article has been invented which exhibits improved fluid management.

SUMMARY OF THE INVENTION

Briefly, this invention relates to an absorbent article which exhibits improved fluid management. The absorbent article includes an absorbent having distally spaced ends and a longitudinally extending central axis. The absorbent also has first and second oppositely aligned surfaces. A bicomponent cover encloses the first surface of the absorbent and includes first and second materials. The first material has openings formed therein and is aligned along the longitudinal central axis of the absorbent. The second material is a nonperforated, nonwoven web which is aligned and/or secured to the first material and provides a soft material adjacent to the user's thighs. The absorbent article also includes separation means for controlling dispersion of body fluid downward, in the z direction, away from the bicomponent cover. The separation means is positioned between the first material and the absorbent. The absorbent article further includes a liquid-impermeable baffle, positioned below the second surface of the absorbent, which functions to prevent fluid from leaking out of the absorbent and soiling an adjacent undergarment.

The general object of this invention is to provide an absorbent article which exhibits improved fluid management. A more specific object of this invention is to provide an absorbent article having an improved level of dryness by utilizing a separation means which cooperates with the first material of the cover.

Another object of this invention is to provide a sanitary napkin with separation means for directing body fluid downward, in the z direction, away from the bicomponent cover.

A further object of this invention is to provide an absorbent article which is relatively inexpensive to manufacture, yet provides superior performance.

Still another object of this invention is to provide an absorbent article which utilizes a bicomponent cover constructed of an apertured first material, consisting of an extrusion-coated nonwoven material or a thermoplastic film, which is bonded to a second material, such as a nonapertured, nonwoven web.

Other objects and advantages of the present invention will become more apparent to those skilled in the art in view of the following description and the accompanying drawings.

DETAILED DESCRIPTION OF THE PREFERRED EMBODIMENT

Figure 1:
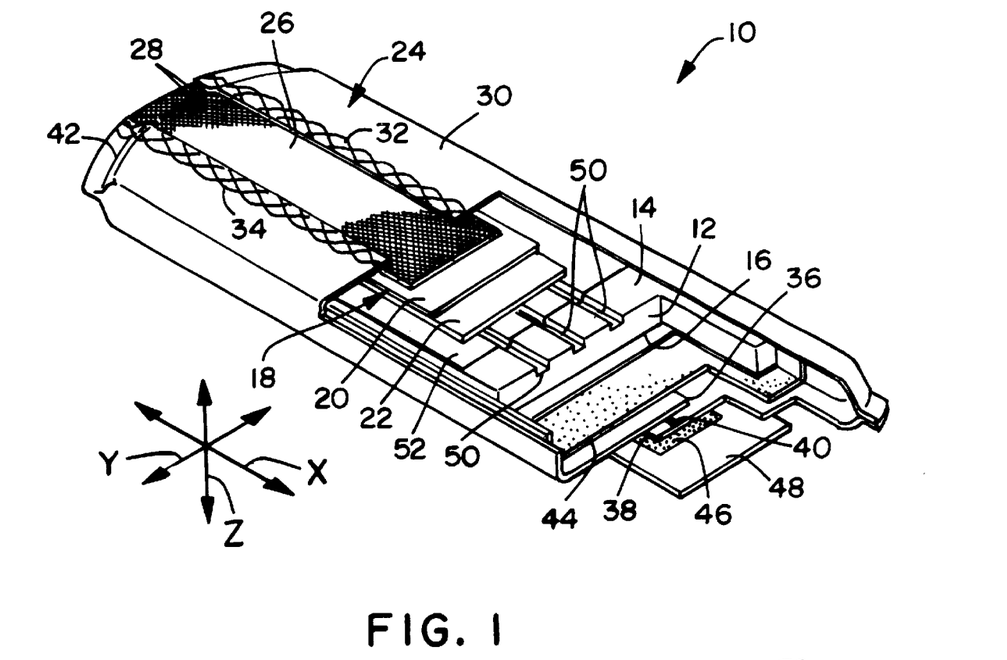
FIG. 1 is a perspective view of an absorbent article exhibiting improved fluid management by utilizing a bicomponent cover in combination with separation means.

Referring to FIG. 1, an absorbent article 10, in the form of a sanitary napkin, is shown having a multi-layered construction. Although the absorbent article 10 is depicted as a sanitary napkin, it could be a diaper, a catamenial pad, a pantiliner, training pants, an incontinent garment, or the like. The absorbent article 10 is a narrow, elongated member with distally spaced ends. The particular shape of the absorbent article 10 can vary with the most common profiles being a narrow rectangular shape, an hourglass shape, an oval shape or a racetrack shape. For purposes of discussion, the length of the absorbent article 10 will be described as extending along the x axis, the width extending along the y axis, and the depth extending along the z axis.

The absorbent article 10 includes an absorbent 12 having first and second oppositely aligned surfaces 14 and 16, respectively, and a longitudinally extending central axis x—x. The absorbent 12 can be made from natural or synthetic fibers, including cellulose fibers, surfactant-treated meltblown fibers, wood pulp fibers, regenerated cellulose or cotton fibers, or coform, which is a blend of pulp and synthetic meltblown fibers. The preferred absorbent material can vary. The preferred absorbent materials, when incorporated into a sanitary napkin, are wood pulp fluff and coform.

The absorbent 12 can contain a hydrocolloidal material, commonly referred to as a superabsorbent. Superabsorbent is normally added to increase the amount of fluid which the absorbent can contain and also to increase fluid retention capability. The absorbent 12 can also be formed as a laminate structure having a superabsorbent material incorporated therein.

Figure 4:
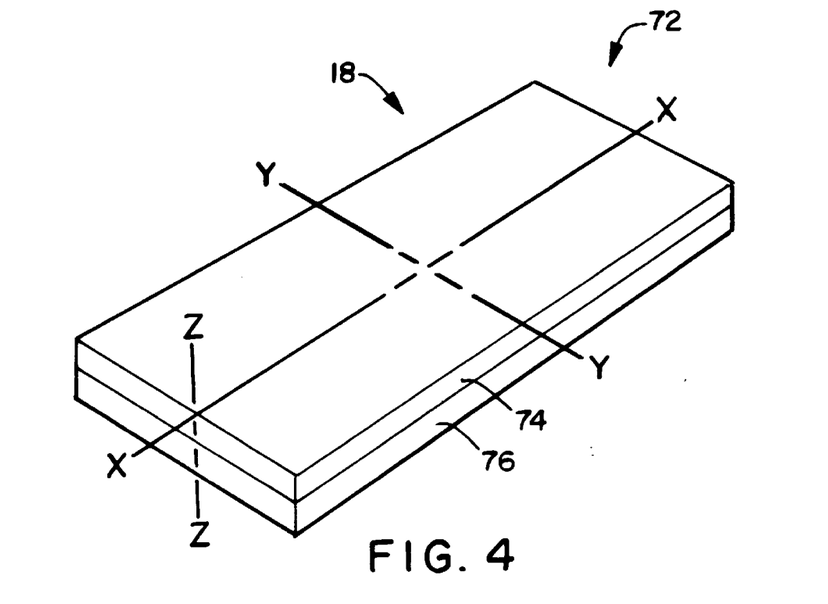
FIG. 4 is a perspective view of the separation means shown in FIG. 1 depicting upper and lower portions formed from two different materials.

Positioned adjacent to, and in intimate contact with, the first surface 14 of the absorbent 12 is a separation means 18. The separation means 18 functions to direct body fluid downward, in the z direction, into the absorbent 12. The separation means 18 can consist of one or more layers. When one layer is present, the separation means 18 can direct the body fluid downward, in the z direction, as well as in the x and/or y direction, if desired. In FIG. 1, the separation means 18 is shown as having two vertically aligned portions or layers 20 and 22 positioned along the longitudinally extending central axis x—x of the absorbent 12. The upper portion 20 is in intimate contact with a portion of a bicomponent cover 24 and can be a material like spunbond, foam or a bonded carded web. The upper portion 20 primarily directs the body fluid downward, in the z direction, into the lower portion 22. The lower portion 22 can be a material like hydroentangled fluff pulp, coform, tissue, fluff pulp or meltblown. The lower portion 22 primarily directs the body fluid outward, in both the x and y directions. The body fluid is thereby dispersed across a larger surface area of the absorbent 12, and this can reduce the amount of time needed for the absorbent 12 to take up or receive the fluid. This dual function enhances the ability of the absorbent article 10 to move the body fluid quickly down into the absorbent 12.

The separation means 18 can be an elongated strip having a thickness of less than about 3 millimeters and preferably between about 0.1–1.5 millimeters. The separation means 18 can be of varying lengths and widths. The length can be greater than, equal to, or less than, the length of the absorbent 12. Generally, for sanitary napkins, the length should be at least 50% of the length of the absorbent 12. For diapers, training pants and incontinent garments, the length should be greater than about 3 inches (76.3 mm). The width of the separation means 18 can also vary. For sanitary napkins, the width can range from between about 0.25–3.0 inches (6 mm–76.3 mm), preferably about 0.75–2.5 inches (19 mm–64 mm), and most preferably about 1.0–2.0 inches (25.4 mm–50.8 mm). Generally, for feminine products, a width of about 25–95%, and preferably about 25–60%, of the width of the article is acceptable. For diapers, training pants and incontinent garments, a width of less than about 5.0 inches (127 mm) is sufficient.

A bicomponent cover 24 is positioned over the separation means 18 and at least partially encloses the absorbent 12. In FIG. 1, the bicomponent cover 24 is overlapped upon itself at the surface which faces the undergarment. The bicomponent cover 24 includes a first material 26 and a second material 30. The first material 26 can be an extrusion-coated nonwoven (ECNW), an apertured thermoplastic film, an extruded netting, a laminated film composite or a film like material that is apertured, apertured foam material or apertured meltblown material. An extrusion-coated nonwoven can be formed, for example, by extruding a molten polymer film, such as polypropylene or polyethylene or a blend thereof, onto a base sheet or substrate. The substrate can also be polypropylene, polyethylene or a blend thereof. When the first material 26 is a thermoplastic film, it can be a polyolefin, such as polyethylene. The thermoplastic film can be perforated or apertured by being subjected to a needling or slitting operation. The film can also be a laminate composite or a nonwoven composite which has been perforated after it has been formed into a laminate.

The following companies commercially sell various kinds of films or film making processes:

---
Smith & Nephew Plastic, Ltd.
Gilberdyke, Brough
North Humderside HU15 2TD
United Kingdom
Applied Extrusion Technologies, Inc.
P.O. Box 582
Middleton, DE 19709
Fameccanica
Fraz Sambuceto
I-66020 San Giovanni Teatino
Italy
LCL Manufacturing PTE, LTD.
16 Pandan Rd.
Singapore 2260
---

The first material 26 extruded be a net, an embossed net, an extruded netting or a net formed from strands of filaments or threads. Examples of covers constructed of netting are taught in U.S. Pat. Nos. 2,295,439; 2,564,689; 2,900,980 and 4,741,941. These patents are incorporated by reference and made a part hereof. The open spaces between the filaments or threads of the netting serve the same function as the apertures or perforations formed through a thermoplastic film. The first material 26 can also be a foam material having a plurality of apertures formed therethrough.

The first material 26 has a plurality of apertures 28 formed therethrough. The apertures 28 can be uniformly or randomly arranged and can be sized to meet one's particular needs. When positioned on the absorbent article 10, the first material 26 preferably is aligned along the longitudinal central axis x—x of the absorbent 12. However, it should be noted that for diapers, training pants, and the like, it may be advantageous to align the first material 26 along the transverse central axis y—Y of the absorbent.

The first material 26 can be an elongated strip having a thickness of less than about 2 millimeters and preferably between about 0.05–2.0 millimeters. The first material 26 can vary in length and width. A length equal to, or less than, the length of the absorbent article 10 is preferred. Generally, for sanitary napkins, the length can vary between about 1–15 inches (25.4 mm–381 mm) and preferably is greater than about 2.0 inches (50.8 mm). For diapers, training pants, and incontinent garments, the length can vary between 1–30 inches (25.4 mm–304.8 mm) and preferably is greater than about 2.0 inches (50.8 mm).

The width of the first material 26 can also vary. For sanitary napkins, the width can range between about 0.25–3.0 inches (6.4 mm–76.2 mm), preferably about 0.75–2.5 inches (19 mm–63.5 mm), and most preferably about 1.0–2.0 inches (25.4 mm–50.8 mm). Generally, for feminine products, a width of about 25–95%, and preferably about 25–60%, of the width of the article is acceptable. For diapers, training pants and incontinent garments, a width of about 5–95%, and preferably less than about 5.0 inches (127 mm), is acceptable. It should be noted that the first material 26 can have a length greater than, equal to, or less than, the length of the separation means 18 and can have a width which is greater than, equal to, or less than, the width of the separation means 18. However, by sizing both elements with approximately the same length and width dimensions, one may be able to simplify the manufacturing process.

The first material 26 is positioned above the upper surface of the separation means 18 and can be directly bonded thereto to facilitate a more efficient fluid transfer therebetween. The first material 26 constitutes the primary fluid-receiving region of the bicomponent cover 24 and is designed to be positioned directly beneath the principal point of discharge from the human body. The discharge orifice can be the urethra, the vaginal orifice, or the anus, and the bodily discharge can include urine, blood, menses and other excrements discharged at various times, such as during a bowel movement or during a menstrual period.

The first material 26 can have a three-dimensional (3-D) profile to give it extra bulk and enhance its functionality. One way to obtain a 3-D profile is to emboss the material between the nip of a pair of rollers.

The second material 30 of the bicomponent cover 24 is a liquid-permeable, nonwoven web which is nonapertured. The second material 30 can be perforated or apertured, if desired, but is not necessary. The second material 30 provides softness against the skin of the wearer of the absorbent article 10 and can be formed from a fibrous material made from fusible polymeric fibers or filaments. Polypropylene spunbond material, bonded carded webs, thermally bonded carded webs, spunbond webs of bicomponent fibers and bonded carded webs of bicomponent fibers work well. The second material 30 can be also be formed from any of the following polymers or combination thereof: polyamides, polyesters, polyolefins, polyvinyl acetate, polyvinyl chloride, polyvinyl alcohol, cellulose acetate, viscose, and the like.

When the second material 30 is a soft nonwoven web, it should be formed from a uniform web having a denier of about 1.5 or greater. Such a nonwoven material is linear drawn spunbond, which is described in U.S. Pat. No. 340,563 issued to Appel et al. This patent is hereby incorporated by reference and made a part hereof. Various kinds of nonwoven webs are manufactured by Kimberly-Clark Corporation, 401 N. Lake street, Neenah, Wis. 54956.

Referring again to FIG. 1, the second material 30 is secured or bonded to the longitudinal side edges of the first material 26 to form seals 32 and 34. The process of bonding the first and second materials 26 and 30, respectively, together can include a mechanical attachment, an adhesive, a thermal bond, pressure bonding or a combination of both heat and pressure. The bond can also be formed by ultrasonics. Ultrasonics involves technology which utilizes ultrasonic sound to form a bond between two materials. Other means of attaching the two materials together can also be used.

It should be noted that the first material 26 can be directly bonded to the second material 30 before the apertures 28 are formed therethrough, or vice versa. Likewise, the bicomponent cover 24 can be constructed off-line and then assembled into the absorbent article 10, or it can be constructed on-line.

The second material 30 is secured to the first material 26 and forms a secondary fluid-receiving region of the bicomponent cover 24. The second material 30 is spaced away from the principal point of discharge of body fluid which the absorbent article 10 is designed to receive. It should be noted that, even though the nonwoven web 30 is designated as the secondary fluid-receiving region of the cover 12, it still has the ability to allow fluid to pass through it and down into the absorbent 12. The rate at which the fluid can pass, commonly referred to as the "fluid pass through rate," is not as rapid as through the perforated first material 26. Accordingly, a vast majority of the body fluid, under normal conditions, will pass down into the absorbent 12, through the first material 26.

The bicomponent cover 24 cooperates with the separation means 18 to provide rapid intake of the body fluid into the absorbent 12. This significantly enhances fluid absorbency and distribution. The direct contact between the bicomponent cover 24 and the separation means 18 also provides a synergistic effect which enhances dryness and, thereby, provides a dry surface next to the user's skin. The bicomponent cover 24 can be constructed with a first material 26 having openings formed therein to promote rapid fluid intake and a second material 30 which is soft to the touch and which has the ability to mask stains. The separation means 18 should assist in masking stains and control the area which does exhibit fluid stains. From the consumer's perspective, the bicomponent cover 24 should be white or opaque to indicate cleanliness, while the separation means 18 can be colored. Peach and blue are two colors which are well received. The color of the separation means 18 will assist in masking stains, especially blood stains, which may form as the body fluid dries on the absorbent 12.

As shown in FIG. 1, the longitudinal free edges 36 and 38 of the bicomponent cover 24 are secured together by a construction adhesive 40 on the garment-facing side of the absorbent article 10. The bicomponent cover 24 is also sealed at its distally spaced ends 42 (one of which is shown) to form a complete enclosure around the absorbent 12. The end seals 42 can be formed with ultrasonics, by using heat and/or pressure, or by an adhesive. It should be noted that the first material 26 forms a smaller portion of the exposed surface area of the bicomponent cover 24 than the second material 30. Stated another way, the second material 30 occupies a larger portion of the exposed surface area of the bicomponent cover 24 than the first material 26. This size difference can reduce the overall cost of manufacturing the absorbent article 10, since the first material 26 is typically more expensive than the second material 30.

Referring again to FIG. 1, the absorbent article 10 further includes a liquid-impermeable baffle 44 positioned adjacent to and below the second surface 16 of the absorbent 12. The baffle 44 is enclosed by the bicomponent cover 24 and functions to prevent body fluid, absorbed by the absorbent 12, from leaking out and soiling or staining an adjacent undergarment. The liquid-impermeable baffle 44 can be made from a micro-embossed polymeric film, such as polyethylene or polypropylene, or it can be made from bicomponent films. A preferred material is polyethylene.

A garment attachment adhesive 46 is secured to an external surface of the bicomponent cover 24 approximate the longitudinal seal line 40. The garment attachment adhesive 46 is designed to secure and hold the absorbent article 10 to an interior surface of an adjacent undergarment. The garment attachment adhesive 46 is covered by a removable peel strip 48. The peel strip 48 is typically formed of paper and is positioned over the garment attachment adhesive 46 to protect it from becoming contaminated by foreign debris prior to use. The peel strip 48 is designed to be removed by the user when she is ready to attach the sanitary napkin to the interior surface of her underwear.

It should be noted that diapers, training pants and incontinent garments usually employ strips of elastic tape to hold the article around the torso. Because of this, the garment attachment adhesive 46 and peel strip 48 may not be needed. Furthermore, absorbent articles such as diapers are designed to function by themselves, and therefore they are not worn inside an undergarment, as is the case for sanitary napkins.

FIG. 1 also shows several longitudinal grooves or channels 50 formed in the upper surface of the absorbent 12. The grooves or channels 50 can be formed by densifying certain areas, such as by embossing. The grooves or channels 50 serve a number of functions, the primary one being to provide flexible longitudinal lines on which the absorbent 12 can bend. The flexible lines or fold lines act to guide the deformation of the absorbent 12 during use and enable the absorbent 12 to acquire a typical "W" fold. The grooves or channels 50 also function to move the body fluid along the x—x axis and, thereby, minimize side leakage. Furthermore, the densified areas of the absorbent 12 located below the grooves or channels 50 tend to attract the body fluid and channel it lengthwise. The grooves or channels 50 are also beneficial when a large amount of fluid has been discharged onto the absorbent article 10 in a short period of time. Sometimes, the amount of body fluid which impinges on the absorbent 12 is greater than the absorbent is capable of absorbing. In these instances, the grooves 50 can act as temporary reservoirs which hold the fluid until it can be absorbed. This provides a backup to the distribution portion of the separation means 18, which can also temporarily retain body fluid. When the body fluid is in the grooves 50, it is spaced away from the bicomponent cover 24 by the separation means 18, and this allows the bicomponent cover 24 to remain dry. Both the bicomponent cover 24 and the separation means 18 are designed to minimize fluid transfer in the upward or reverse direction. This feature, commonly referred to as "a low rewet value," is important to providing a dry feel to the cover 24.

The following rewet data was generated using 8 cubic centimeters of distilled water at 1 psi pressure to show the effect of maintaining a dry cover. The data in Table 1 lists rewet values for the first material of the bicomponent cover when used in conjunction with a separation layer. The data in Table 2 lists rewet values for the first material of the bicomponent cover when used without a separation layer. The data in Table 3 lists rewet values for the second material of the bicomponent cover when used without the separation layer. A low number represents low rewet properties and, therefore, indicates that the cover will remain dry. A dry cover is very desirable.

A unique feature of this invention is the synergistic effect obtained when the first material 26 of the bicomponent cover 24 is placed adjacent to the separation means 18. When the separation means 18 is positioned below the bicomponent cover 24, the level of dryness is very good, as indicated by the rewet values in Table 1. By comparison, the rewet values in Table 2, which represent the cover material without the separation means 18 positioned below it, are considerably higher. Furthermore, one will notice that, when the first material of the bicomponent cover is an apertured thermoplastic film, see items 2 and 3 in Tables 1 and 2, a significant improvement is obtained by using the separation means 18. The extrusion-coated nonwoven material, the first material listed in Tables 1 and 2, does not experience such a noticeable reduction in rewet values when the separation means 18 is present. One can speculate that the reason for this may be that the extrusion-coated nonwoven material always delivers a relatively high degree of dryness.

Referring to Table 3, the rewet values for the second material of the bicomponent cover without the separation layer are shown. For each material tested, a high rewet value was obtained, which indicates the material did not exhibit good dryness. The values obtained for the first material in combination with the separation layer were much lower than any of the values obtained for the second materials without separation means. This indicates that the combination of a first material and a separation layer significantly improves the ability to deliver dryness when compared against a second material without a separation layer. This is important in the performance of a sanitary product, because the primary area insulted by body fluid is the first material. As a result, improved dryness can be delivered through the combination of the first material when used in conjunction with the separation means.

A comparison between the values of the material in Table 1 against the values of the material in Table 3 indicates the following: a) in Table 1, materials 1 and 3 are the wettest and in Table 3, material 3 is the driest; and b) a comparison of these values reveals that the rewet value for material 1 or 3 in Table 1 is approximately 80% lower than the rewet value for material 3 in Table 3. Preferably, the first material used in conjunction with a separation means should have a rewet value that is at least 10% lower then the rewet value of the second material without the separation means.

TABLE 1

| | FIRST MATERIAL WITH SEPARATION MEANS | REWET (gm) |
|---|---|---|
| Material 1 | Extrusion-Coated Nonwoven (ECNW) 0.75 mil polypropylene (PP) film/0.8 ounces per square yard (osy) PP spunbond 1.5 osy PP spunbond-separation means | 0.08 |
| Material 2 | Two dimensional netting 1.5 osy PP spunbond-separation means | 0.07 |
| Material 3 | Three dimensional apertured film 1.5 osy PP spunbond-separation means | O.08 |

TABLE 2

| | FIRST MATERIAL WITHOUT SEPARATION MEANS | REWET (gm) |
|---|---|---|
| Material 1 | Extrusion-Coated Nonwoven (ECNW) 0.75 mil PP film/ 0.8 osy PP spunbond | 0.04 |
| Material 2 | Two dimensional netting 24 gsm, 0.07 mm bulk | 2.11 |
| Material 3 | Three dimensional apertured film 35 gsm, 0.65 mm bulk | 0.60 |

TABLE 3

| | SECOND MATERIAL WITHOUT SEPARATION MEANS | REWET (gm) |
|---|---|---|
| Material 1 | SPUNBOND 0.4 osy polypropylene spunbond (5 denier) | 1.92 |
| Material 2 | SPUNBOND 0.6 osy 97% polypropylene/3% polyethylene spunbond (5 denier) | 1.52 |
| Material 3 | BONDED CARDED WEB 48 grams per square meter polypropylene, 75% hydrophobic, 25% hydrophilic, thermally bonded | 0.40 |

TABLE 3-continued

| | SECOND MATERIAL WITHOUT SEPARATION MEANS | REWET (gm) |
|---|---|---|
| Material 4 | THERMAL BONDED CARDED WEB 22 grams per square meter polypropylene, thermally bonded | 1.63 |

Referring again to FIG. 1, the absorbent article 10 has an optional tissue layer 52 wrapped about the absorbent 12. The tissue 52 is beneficial when superabsorbent particles are integrated into the absorbent 12. The tissue layer 52 provides a protective barrier to prevent the superabsorbent particles from migrating out of the absorbent 12 during transport and handling of the absorbent article 10. During shipment, it is common for the absorbent article 10 to be subjected to shakes and bumps, and this action can cause the superabsorbent particles to separate from the absorbent 12.

Figure 2:
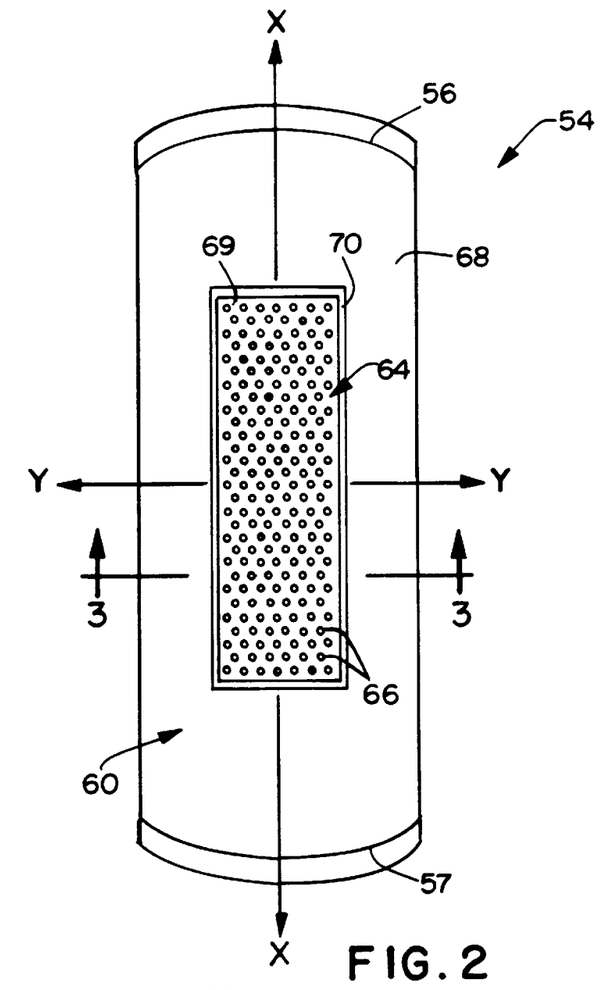
FIG. 2 is a top view of another embodiment showing an absorbent article having a bicomponent cover wherein an apertured first material is completely surrounded by a second material.
Figure 3:
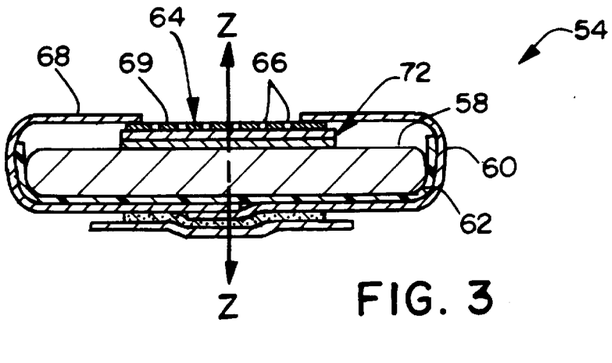
FIG. 3 is a cross-sectional view of the absorbent article shown in FIG. 2 taken along line 3—3 depicting the cover spaced apart from the primary absorbent layer so as to better show the layers positioned therebetween.

Referring to FIGS. 2 and 3, an absorbent article 54, in the form of a feminine napkin, is shown having distally spaced ends 56 and 57 and a longitudinally extending central axis x—x. The absorbent article 54 includes an absorbent 58 sandwiched between a liquid-permeable, bicomponent cover 60 and a liquid-impermeable baffle 62. The bicomponent cover 60 contains a first material 64 and a second material 68. The first material 64 can be either an extrusion-coated nonwoven material or a thermoplastic film. The first material 64 has a plurality of apertures 66 formed therethrough. The second material 68 can be a nonperforated, nonwoven web which completely surrounds the first material 64. The second material 68 is secured at 70, such as by bonding, to at least a substantial portion of the outer periphery of the first material 64. The bond can be formed by adhesive or ultrasonics. The bond 70 can be continuous or discontinuous about the outer periphery of the first material 64.

In FIG. 2, the first material 64 is shaped as a narrow rectangle having a length about 50–90% of the length of the absorbent article 54. By surrounding the first material 64 with the second material 68, a window configuration is formed on the body-facing surface of the bicomponent cover 60. In use, the first material 64 would be situated in alignment with the fluid discharge orifice and function as the primary fluid-receiving region of the bicomponent cover 60.

The absorbent article 54 also contains separation means 72 positioned between the bicomponent cover 60 and the upper surface of the absorbent 58. Preferably, the separation means 72 is aligned along the longitudinal central axis x—x of the absorbent article 54. The separation means 72 is shown constructed out of at least two different kinds of materials, although a single layer can also be used. The separation means 18 has an upper portion 74 and a lower portion 76. The upper portion 74 can be formed from a material like spunbond or a bonded carded web and serves to direct the body fluid primarily downward, in the z direction, away from the bicomponent cover 60 and into the lower portion 76. The lower portion 76 can be formed from a material like hydroentangled fluff pulp, coform or meltblown and serves to distribute the body fluid primarily in the x and y directions. By dispersing the body fluid over a greater surface area, it can more quickly be absorbed by the absorbent 58. Furthermore, the ability to rapidly transfer body fluid downward into the absorbent 58, where it can be retained, does assist in maintaining a dry cover adjacent to the user's body. These features are desirable from the consumer's viewpoint.

Figure 5:
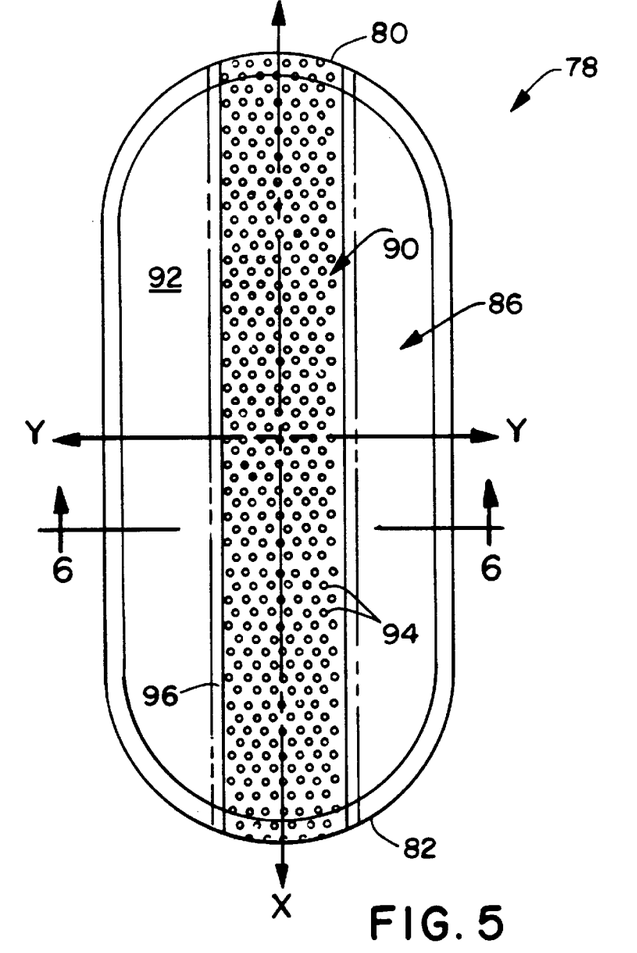
FIG. 5 is a top view of another embodiment showing an absorbent article having a bicomponent cover with the first material extending the entire length of the absorbent article.
Figure 6:
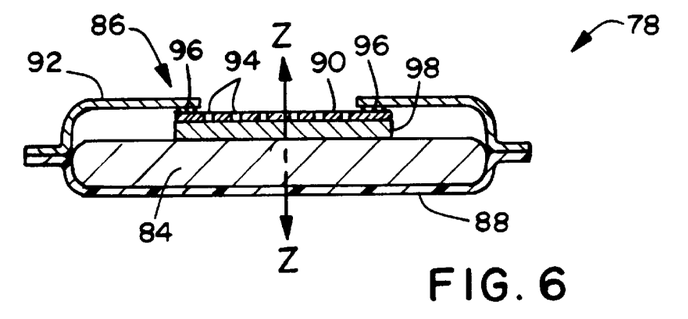
FIG. 6 is a cross-sectional view of the absorbent article shown in FIG. 5 taken along line 6—6 wherein the separation means is a single layer and the cover is spaced apart from the primary absorbent layer so as to better show the layers positioned therebetween.

Referring to FIGS. 5 and 6, another embodiment of an absorbent article 78 is shown in the form of a sanitary napkin. The absorbent article 78 has distally spaced ends 80 and 82 and a longitudinally extending central axis x—x. The absorbent article 78 includes an absorbent 84 sandwiched between a liquid-permeable, bicomponent cover 86 and a liquid-impermeable baffle 88. The bicomponent cover 86 is preferably secured or bonded to the baffle 88 to completely enclose the absorbent 84. The bicomponent cover 86 contains a first material 90 and a second material 92. The first material 90 can be an extrusion-coated nonwoven material, a perforated thermoplastic film or a netting. The first material 90 is a narrow rectangle having a length approximately equal to the length of the absorbent article 78 and has a plurality of apertures 94 formed therethrough. In use, the first material 90 would be situated in alignment with the fluid discharge orifice and functions as the primary fluid-receiving region of the bicomponent cover 86.

The second material 92 is a nonperforated, nonwoven web which is secured to the first material 90. The second material 92 is bonded, such as by an adhesive 96, to at least a portion of the outer periphery of the first material 90. The adhesive bond 96 can be continuous or discontinuous along the longitudinal sides of the first material 90. In use, the second material 92 would be spaced away from the fluid discharge orifice and functions as the secondary fluid-receiving region of the bicomponent cover 86.

The absorbent article 78 also contains separation means 98 positioned between the bicomponent cover 86 and the upper surface of the absorbent 78 and aligned along the longitudinal central axis x—x. The separation means 98 is a single layer constructed of a material, like spunbond or a bonded carded web, and serves to direct the body fluid downward, in the z direction, away from the bicomponent cover 86. This ability to rapidly transfer body fluid downward into the absorbent 84, where it can be retained, does assist in maintaining a dry cover adjacent to the user's body. These features are desirable from the consumer's viewpoint.

Figure 7:
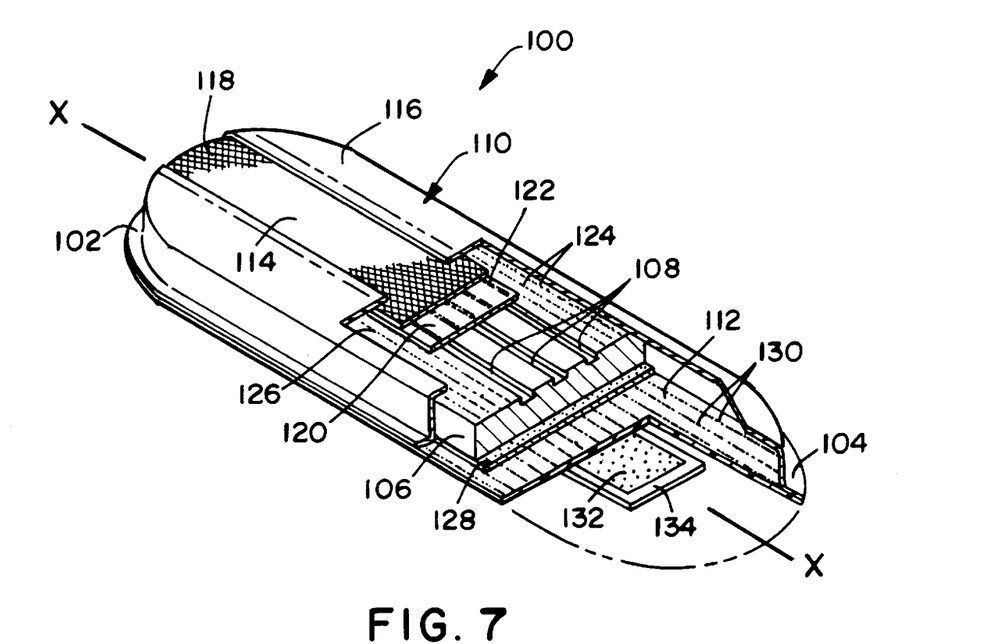
FIG. 7 is a perspective view of an absorbent article exhibiting improved fluid management by utilizing a bicomponent cover having a first material secured to the separation means.

Referring to FIG. 7, another embodiment of an absorbent article 100 is shown in the form of a sanitary napkin. The absorbent article 100 has distally spaced ends 102 and 104 and a longitudinally extending central axis x—x. The absorbent article 100 includes an absorbent 106 having one or more longitudinal grooves 108 formed therein. The grooves 108 serve the same function as the grooves 50 shown in FIG. 1. The absorbent 106 is sandwiched between a liquid-permeable, bicomponent cover 110 and a liquid-impermeable baffle 112. The bicomponent cover 110 is preferably secured or bonded to the baffle 112 to completely enclose the absorbent 106. The bicomponent cover 110 contains a first material 114 and a second material 116. The first material 114 can be either an extrusion-coated nonwoven material or a thermoplastic film. The first material 114 is a narrow rectangle having a length approximately equal to the length of the absorbent article 100 and has a plurality of apertures 118 formed therethrough. In use, the first material 114 would be situated in alignment with the fluid discharge orifice and functions as the primary fluid-receiving region of the bicomponent cover 110.

The second material 116 is a nonperforated, nonwoven web which can partially overlap the longitudinal side edges of the first material 114. The second material 116 is not bonded to the first material 114 in this embodiment. In use, the second material 116 would be spaced away from the fluid discharge orifice and functions as the secondary fluid-receiving region of the bicomponent cover 110.

The absorbent article 100 also contains separation means 120 positioned between the bicomponent cover 110 and the upper surface of the absorbent 106. The separation means 120 is aligned along the longitudinal central axis x—x. The separation means 120 is a single layer constructed of a material, like spunbond or a bonded carded web, and serves to direct the body fluid downward, in the z direction, away from the bicomponent cover 110. This ability to rapidly transfer body fluid downward into the absorbent 106, where it can be retained, does assist in maintaining a dry cover adjacent to the user's body. The separation means 120 is bonded directly to the first material 114 by construction adhesive 122, while the second material 116 is bonded by construction adhesive 124 and 126 to the top surface of the absorbent 106. By securing the separation means 120 directly to the first material 114, better fluid transfer between the two materials can be obtained. Likewise, securing the second material 116 directly to the absorbent 106 can improve the dryness of the entire cover and will assist in preventing rewet.

The absorbent article 100 also contains a layer of tissue 128 and a layer of construction adhesive 130 positioned between the absorbent 106 and the liquid-impermeable baffle 112. The adhesive 130 ensures that the baffle 112 will remain in intimate contact with the absorbent 106. Attached to the exterior surface of the baffle 112 is a strip of garment adhesive 132 which is covered by a releasable peel strip 134. Before use, the peel strip 134 is removed, and the absorbent article is positioned against the inner crotch portion of an undergarment. The garment adhesive 132 will hold the absorbent article 100 securely to the undergarment.

Figure 8:
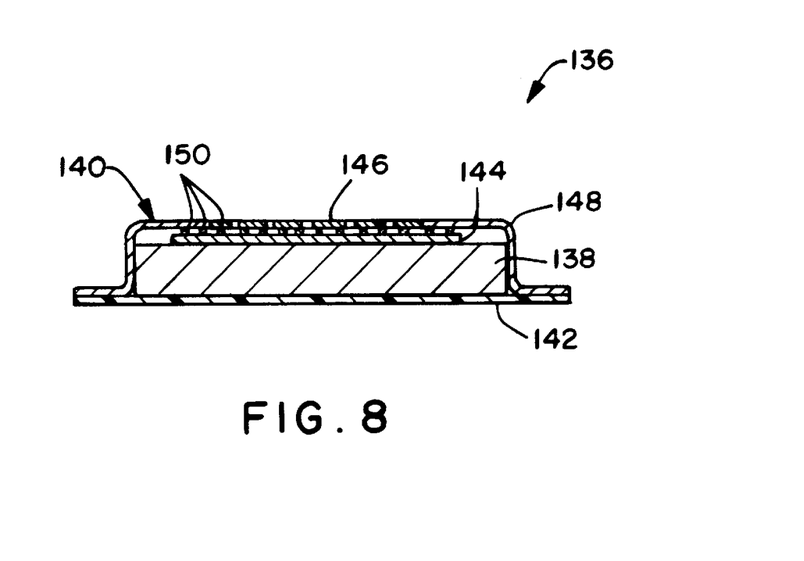
FIG. 8 is a cross-sectional view of still another embodiment wherein the bicomponent cover contains a first material and a second material, each of which is directly bonded to the separation means and the cover is spaced apart from the primary absorbent layer so as to better show the layers positioned therebetween.

Referring to FIG. 8, a cross-sectional view of another embodiment of an absorbent article 136 is shown. The absorbent article 136 includes an absorbent 138 positioned between a liquid-permeable, bicomponent cover 140 and a liquid-impermeable baffle 142. Separation means 144 is positioned between the top surface of the absorbent 138 and the bicomponent cover 140. The separation means 144 functions to direct body fluid downward, in the z direction, away from the bicomponent cover 140 so as to keep it dry. The bicomponent cover 140 includes an apertured first material 146 and a nonapertured second material 148, both of which are directly bonded to the separation means 144 by a construction adhesive 150. The construction adhesive can be applied in a swirl pattern, in straight lines or as an intermittent thin coating over a portion of the top surface of the separation means 144. In this embodiment, the first material 146 is not overlapped or bonded to the second material 148, but instead the first and second materials 146 and 148, respectively, are aligned in an abutting relationship along their longitudinal edges.

While the invention has been described in conjunction with specific embodiments, it is to be understood that many alternatives, modifications and variations will be apparent to those skilled in the art, in light of the aforegoing description. Accordingly, this invention is intended to embrace all such alternatives, modifications and variations which fall within the spirit and scope of the appended claims.

We claim:

1. An absorbent article comprising;
   a) an absorbent;
   b) a bicomponent cover at least partially enclosing said absorbent, said bicomponent cover including a first material having openings formed therethrough and which is aligned along the longitudinal central axis of said absorbent and a nonapertured second material secured to at least a portion of the outer periphery of said first material, said second material being different from said first material; and c) separation means for controlling dispersion of body fluid downward, in the z-direction, away from said bicomponent cover, said separation means being positioned between only said first material and said absorbent.

2. The absorbent article of claim 1 wherein said first material is a strip of apertured thermoplastic film having a thickness of less than about 2 millimeters and a width of greater than about 12 millimeters, said second material being a nonwoven web.

3. The absorbent article of claim 1 wherein said absorbent has a first surface and a second surface aligned opposite to said first surface, and positioned below said second surface is a liquid-impermeable baffle which cooperates with said cover to enclose said absorbent.

4. The absorbent article of claim 1 wherein said first material in conjunction with said separation means has a rewet value which is at least 10% lower than the rewet value of said second material without said separation means.

5. An absorbent article comprising:
a) an absorbent having distally spaced ends and a longitudinally extending central axis, said absorbent having first and second oppositely aligned surfaces, with said first surface having at least one longitudinal channel formed therein;
b) a bicomponent cover enclosing at least said first surface of said absorbent, said bicomponent cover including a first material having a plurality of apertures formed therethrough and sized to extend at least between said distally spaced ends of said absorbent, and a nonperforated second material secured to said first material, said second material being different from said first material;
c) separation means for controlling dispersion of body fluid downward, in the z-direction, away from said bicomponent cover to enable said fluid to be quickly absorbed by said absorbent, said separation means being positioned between only said first material and said first surface of said absorbent and being aligned along said longitudinally extending central axis of said absorbent; and
d) a liquid-impermeable baffle positioned adjacent to said second surface of said absorbent.

6. The absorbent article of claim 5 wherein said first material is a strip of thermoplastic film having a thickness of less than about 2 millimeters and a width of greater than about 12 millimeters and said second material is a nonwoven web.

7. The absorbent article of claim 6 wherein said nonwoven web is bonded to at least a portion of the outer periphery of said thermoplastic film.

8. The absorbent article of claim 5 wherein said second material is ultrasonically bonded to said first material.

9. The absorbent article of claim 5 wherein said second material is thermally bonded to said first material.

10. The absorbent article of claim 5 wherein said second material is adhesively bonded to said first material.

11. The absorbent article of claim 5 wherein said separation means has two distinct portions, an upper portion which functions to direct body fluid downward, in the z direction, away from said cover, and a lower portion which functions to disperse body fluid in the x and y directions to enable said fluid to contact a larger area of said absorbent.

12. The absorbent article of claim 5 wherein said separation means is bonded to said first material to control fluid transfer therebetween.

13. The absorbent article of claim 11 wherein said separation means contains at least two distinct materials, one of said materials being spunbond.

14. The absorbent article of claim 11 wherein said separation means is a laminate comprised of spunbond joined to hydroentangled fluff.

15. The absorbent article of claim 5 wherein said first material in conjunction with said separation means has a rewet value which is at least 10% lower than the rewet value of said second material without said separation means.

16. An absorbent article comprising:
a) an absorbent having distally spaced ends and a longitudinally extending central axis, said absorbent having first and second oppositely aligned surfaces;
b) a bicomponent cover enclosing at least said first surface of said absorbent, said bicomponent cover including a film containing a plurality of apertures formed therethrough, said film being aligned about said longitudinally extending central axis and extending at least between said distally spaced ends of said absorbent, and a nonperforated, nonwoven web secured to and cooperating with said film;
c) separation means for controlling dispersion of body fluid to said absorbent, said separation means having two distinct portions, an upper portion which functions to direct body fluid downward, in the z-direction, away from said bicomponent cover and a lower portion which functions to direct body fluid outward, in the x and y-directions, to enable said body fluid to contact a larger area of said absorbent and be quickly absorbed, said separation means being positioned between only said first material and said first surface of said absorbent; and
d) a liquid-impermeable baffle positioned adjacent to said second surface of said absorbent.

17. The absorbent article of claim 16 wherein said separation means contains at least two separate and distinct materials, one of said materials being spunbond.

18. The absorbent article of claim 16 wherein said separation means is a laminate comprised of spunbond joined to a hydroentangled fluff.

19. The absorbent article of claim 16 wherein said first material in conjunction with said separation means has a rewet value which is at least 10% lower than the rewet value of said second material without said separation means.

20. An absorbent article comprising:
a) an absorbent having first and second oppositely aligned surfaces and a longitudinally extending central axis;
b) a bicomponent cover enclosing at least said first surface of said absorbent, said bicomponent cover including an extrusion-coated nonwoven containing a plurality of apertures formed therethrough, said extrusion-coated nonwoven being aligned about said longitudinally extending central axis and extending at least between said distally spaced ends of said absorbent, and a nonperforated, nonwoven web secured to and cooperating with said extrusion-coated nonwoven, said extrusion-coated nonwoven being different from said nonwoven web;
c) separation means for controlling dispersion of body fluid to said absorbent, said separation means having two distinct portions, an upper portion which functions to direct body fluid downward, in the z-direction, and a lower portion which functions to direct body fluid outward, in the x and y-directions, to enable said body fluid to contact a larger area of said absorbent and be quickly absorbed, said separation means being positioned between only said extrusion-coated nonwoven and said first surface of said absorbent and aligned along said longitudinally extending central axis; and d) a liquid-impermeable baffle positioned adjacent to said second surface of said absorbent.

21. The absorbent article of claim 20 wherein said first material in conjunction with said separation means has a rewet value which is at least 10% lower than the rewet value of said second material without said separation means.

22. An absorbent article comprising;
   a) an absorbent;
   b) a liquid-impermeable baffle;
   c) a liquid-permeable, bicomponent cover cooperating with said baffle to enclose said absorbent, said bicomponent cover including a thermoplastic film containing a plurality of apertures formed therethrough, said film being aligned along the longitudinal central axis of said absorbent and constituting a primary fluid-receiving region of said bicomponent cover, and a nonperforated, nonwoven web secured to at least a portion of the outer periphery of said film, said nonwoven web being different from said thermoplastic film and constituting a secondary fluid-receiving region of said bicomponent cover; and
   d) separation means for controlling dispersion of body fluid downward, in the z-direction, away from said bicomponent cover and outward, in the x and y-directions, to enable said body fluid to contact a larger area of said absorbent, said separation means being positioned between only said thermoplastic film and said absorbent.

23. The absorbent article of claim 22 wherein said first material in conjunction with said separation means has a rewet value which is at least 10% lower than the rewet value of said second material without said separation means.

24. An absorbent article comprising;
   a) an absorbent;
   b) a bicomponent cover at least partially enclosing said absorbent, said bicomponent cover including an apertured first material aligned along the longitudinal central axis of said absorbent and a nonapertured second material, said second material being different from said first material; and
   c) separation means for controlling dispersion of body fluid downward, in the z-direction, away from said bicomponent cover, said separation means being positioned between only said first material and said absorbent and secured to said first material.

25. The absorbent article of claim 24 wherein said second material overlaps a portion of said first material.

26. The absorbent article of claim 24 wherein said first material in conjunction with said separation means has a rewet value which is at least 10% lower than the rewet value of said second material without said separation means.

27. An absorbent article comprising;
   a) an absorbent;
   b) a bicomponent cover at least partially enclosing said absorbent, said bicomponent cover including an apertured first material aligned along the longitudinal central axis of said absorbent and a nonapertured second material, said second material being different from said first material; and
   c) separation means for controlling dispersion of body fluid downward, in the z-direction, away from said bicomponent cover, said separation means being positioned between only said first material and said absorbent and being secured to said first material.

28. The absorbent article of claim 27 wherein said first material in conjunction with said separation means has a rewet value which is at least 10% lower than the rewet value of said second material without said separation means.

29. An absorbent article comprising;
   a) an absorbent;
   b) a bicomponent cover at least partially enclosing said absorbent, said bicomponent cover including a net material having openings located between intersecting strands and which is aligned along the longitudinal central axis of said absorbent and a nonapertured second material secured to at least a portion of the outer periphery of said first material, said second material being different from said net material; and
   c) separation means for controlling dispersion of body fluid downward, in the z-direction, away from said bicomponent cover, said separation means being positioned between only said net material and said absorbent.

30. The absorbent article of claim 29 wherein said first material in conjunction with said separation means has a rewet value which is at least 10% lower than the rewet value of said second material without said separation means.

31. An absorbent article comprising;
   a) an absorbent;
   b) a bicomponent cover at least partially enclosing said absorbent, said bicomponent cover including a first material having openings formed therethrough and which is aligned along the longitudinal central axis of said absorbent and a nonapertured second material secured to at least a portion of the outer periphery of said first material, said second material being different from said first material; and
   c) separation means for controlling dispersion of body fluid downward, in the z-direction, away from said bicomponent cover, said separation means being positioned between only said first material and said absorbent, and said first material in conjunction with said separation means has a rewet value of less than 1.7 grams.

32. An absorbent article comprising:
   a) an absorbent having distally spaced ends and a longitudinally extending central axis, said absorbent having first and second oppositely aligned surfaces, with said first surface having at least one longitudinal channel formed therein;
   b) a bicomponent cover enclosing at least said first surface of said absorbent, said bicomponent cover including a first material having a plurality of apertures formed therethrough and sized to extend at least between said distally spaced ends of said absorbent, and a nonperforated second material secured to said first material, said second material being different from said first material;
   c) separation means for controlling dispersion of body fluid downward, in the z-direction, away from said bicomponent cover to enable said fluid to be quickly absorbed by said absorbent, said separation means being positioned between only said first material and said first surface of said absorbent and being aligned along said longitudinally extending central axis of said absorbent, and said first material in conjunction with said separation means has a rewet value of less than 1.7 grams; and
   d) a liquid-impermeable baffle positioned adjacent to said second surface of said absorbent.

33. An absorbent article comprising:
a) an absorbent having distally spaced ends and a longitudinally extending central axis, said absorbent having first and second oppositely aligned surfaces;
b) a bicomponent cover enclosing at least said first surface of said absorbent, said bicomponent cover including a film containing a plurality of apertures formed therethrough, said film being aligned about said longitudinally extending central axis and extending at least between said distally spaced ends of said absorbent, and a nonperforated, nonwoven web secured to and cooperating with said film;
c) separation means for controlling dispersion of body fluid to said absorbent, said separation means having two distinct portions, an upper portion which functions to direct body fluid downward, in the z-direction, away from said bicomponent cover and a lower portion which functions to direct body fluid outward, in the x and y-directions, to enable said body fluid to contact a larger area of said absorbent and be quickly absorbed, said separation means being positioned between only said first material and said first surface of said absorbent, and said first material in conjunction with said separation means has a rewet value of less than 1.7 grams; and
d) a liquid-impermeable baffle positioned adjacent to said second surface of said absorbent.

34. An absorbent article comprising:
a) an absorbent having first and second oppositely aligned surfaces and a longitudinally extending central axis;
b) a bicomponent cover enclosing at least said first surface of said absorbent, said bicomponent cover including an extrusion-coated nonwoven containing a plurality of apertures formed therethrough, said extrusion-coated nonwoven being aligned about said longitudinally extending central axis and extending at least between said distally spaced ends of said absorbent, and a nonperforated, nonwoven web secured to and cooperating with said extrusion-coated nonwoven, said extrusion-coated nonwoven being different from said nonwoven web;
c) separation means for controlling dispersion of body fluid to said absorbent, said separation means having two distinct portions, an upper portion which functions to direct body fluid downward, in the z-direction, and a lower portion which functions to direct body fluid outward, in the x and y directions, to enable said body fluid to contact a larger area of said absorbent and be quickly absorbed, said separation means being positioned between only said extrusion-coated nonwoven and said first surface of said absorbent and aligned along said longitudinally extending central axis, and said first material in conjunction with said separation means has a rewet value of less than 1.7 grams; and
d) a liquid-impermeable baffle positioned adjacent to said second surface of said absorbent.

35. An absorbent article comprising;
a) an absorbent;
b) a liquid-impermeable baffle;
c) a liquid-permeable, bicomponent cover cooperating with said baffle to enclose said absorbent, said bicomponent cover including a thermoplastic film containing a plurality of apertures formed therethrough, said film being aligned along the longitudinal central axis of said absorbent and constituting a primary fluid-receiving region of said bicomponent cover, and a nonperforated, nonwoven web secured to at least a portion of the outer periphery of said film, said nonwoven web being different from said thermoplastic film and constituting a secondary fluid-receiving region of said bicomponent cover; and
d) separation means for controlling dispersion of body fluid downward, in the z-direction, away from said bicomponent cover and outward, in the x and y-directions, to enable said body fluid to contact a larger area of said absorbent, said separation means being positioned between only said thermoplastic film and said absorbent, and said first material in conjunction with said separation means has a rewet value of less than 1.7 grams.

36. An absorbent article comprising;
a) an absorbent;
b) a bicomponent cover at least partially enclosing said absorbent, said bicomponent cover including an apertured first material aligned along the longitudinal central axis of said absorbent and a nonapertured second material, said second material being different from said first material; and
c) separation means for controlling dispersion of body fluid downward, in the z-direction, away from said bicomponent cover, said separation means being positioned between only said first material and said absorbent and secured to said first material, and said first material in conjunction with said separation means has a rewet value of less than 1.7 grams.

37. An absorbent article comprising;
a) an absorbent;
b) a bicomponent cover at least partially enclosing said absorbent, said bicomponent cover including an apertured first material aligned along the longitudinal central axis of said absorbent and a nonapertured second material, said second material being different from said first material; and
c) separation means for controlling dispersion of body fluid downward, in the z-direction, away from said bicomponent cover, said separation means being positioned between only said first material and said absorbent and being secured to said first material, and said first material in conjunction with said separation means has a rewet value of less than 1.7 grams.

38. An absorbent article comprising;
a) an absorbent;
b) a bicomponent cover at least partially enclosing said absorbent, said bicomponent cover including a net material having openings located between intersecting strands and which is aligned along the longitudinal central axis of said absorbent and a nonapertured second material secured to at least a portion of the outer periphery of said first material, said second material being different from said net material; and
c) separation means for controlling dispersion of body fluid downward, in the z-direction, away from said bicomponent cover, said separation means being positioned between only said net material and said absorbent, and said first material in conjunction with said separation means has a rewet value of less than 1.7 grams.

39. An absorbent article comprising;
a) an absorbent;
b) a bicomponent cover at least partially enclosing said absorbent, said bicomponent cover including a first material having openings formed therethrough and which is aligned along the longitudinal central axis of said absorbent and a nonapertured second material secured to at least a portion of the outer periphery of said first material, said second material being different from said first material; and c) separation means for controlling dispersion of body fluid downward, in the z-direction, away from said bicomponent cover, said separation means being positioned between only said first material and said absorbent, and said first material in conjunction with said separation means has a rewet value of less than 0.1 grams.

40. An absorbent article comprising:

a) an absorbent having a first surface and a longitudinally extending central axis;

b) a bicomponent cover enclosing at least said first surface of said absorbent, said bicomponent cover including a first material having openings formed therethrough and a second material which is secured to said first material, said second material being different from said first material; and c) separation means for controlling dispersion of body fluid downward, in the z-direction, away from said bicomponent cover, said separation means being positioned between only said first material and said first surface of said absorbent and being aligned along said longitudinally extending central axis of said absorbent, and said first material in conjunction with said separation means has a rewet value of less than 0.1 grams.

41. An absorbent article comprising;

a) an absorbent;

b) a bicomponent cover at least partially enclosing said absorbent, said bicomponent cover including an apertured first material aligned along the longitudinal central axis of said absorbent and a nonapertured second material, said second material being different from said first material; and c) separation means for controlling dispersion of body fluid downward, in the z-direction, away from said bicomponent cover, said separation means being positioned between only said first material and said absorbent and secured to said first material, and said first material in conjunction with said separation means has a rewet value of less than 0.1 grams.

42. An absorbent article comprising:

a) an absorbent having distally spaced ends and a longitudinally extending central axis, said absorbent having first and second oppositely aligned surfaces, with said first surface having at least one longitudinal channel formed therein;

b) a bicomponent cover enclosing at least said first surface of said absorbent, said bicomponent cover including a first material having a plurality of apertures formed therethrough and sized to extend at least between said distally spaced ends of said absorbent, and a nonperforated second material secured to said first material, said second material being different from said first material;

c) separation means for controlling dispersion of body fluid downward, in the z-direction, away from said bicomponent cover to enable said fluid to be quickly absorbed by said absorbent, said separation means being positioned between only said first material and said first surface of said absorbent and being aligned along said longitudinally extending central axis of said absorbent, and said first material in conjunction with said separation means has a rewet value of less than 0.1 grams; and d) a liquid-impermeable baffle positioned adjacent to said second surface of said absorbent.

43. An absorbent article comprising:

a) an absorbent having distally spaced ends and a longitudinally extending central axis, said absorbent having first and second oppositely aligned surfaces;

b) a bicomponent cover enclosing at least said first surface of said absorbent, said bicomponent cover including a film containing a plurality of apertures formed therethrough, said film being aligned about said longitudinally extending central axis and extending at least between said distally spaced ends of said absorbent, and a nonperforated, nonwoven web secured to and cooperating with said film;

c) separation means for controlling dispersion of body fluid to said absorbent, said separation means having two distinct portions, an upper portion which functions to direct body fluid downward, in the z-direction, away from said bicomponent cover and a lower portion which functions to direct body fluid outward, in the x and y-directions, to enable said body fluid to contact a larger area of said absorbent and be quickly absorbed, said separation means being positioned between only said first material and said first surface of said absorbent, and said first material in conjunction with said separation means has a rewet value of less than 0.1 grams; and d) a liquid-impermeable baffle positioned adjacent to said second surface of said absorbent.

44. An absorbent article comprising:

a) an absorbent having first and second oppositely aligned surfaces and a longitudinally extending central axis;

b) a bicomponent cover enclosing at least said first surface of said absorbent, said bicomponent cover including an extrusion-coated nonwoven containing a plurality of apertures formed therethrough, said extrusion-coated nonwoven being aligned about said longitudinally extending central axis and extending at least between said distally spaced ends of said absorbent, and a nonperforated, nonwoven web secured to and cooperating with said extrusion-coated nonwoven, said extrusion-coated nonwoven being different from said nonwoven web;

c) separation means for controlling dispersion of body fluid to said absorbent, said separation means having two distinct portions, an upper portion which functions to direct body fluid downward, in the z-direction, and a lower portion which functions to direct body fluid outward, in the x and y-directions, to enable said body fluid to contact a larger area of said absorbent and be quickly absorbed, said separation means being positioned between only said extrusion-coated nonwoven and said first surface of said absorbent and aligned along said longitudinally extending central axis, and said first material in conjunction with said separation means has a rewet value of less than 0.1 grams; and d) a liquid-impermeable baffle positioned adjacent to said second surface of said absorbent.

45. An absorbent article comprising;

a) an absorbent;

b) a liquid-impermeable baffle;

c) a liquid-permeable, bicomponent cover cooperating with said baffle to enclose said absorbent, said bicomponent cover including a thermoplastic film containing a plurality of apertures formed therethrough, said film being aligned along the longitudinal central axis of said absorbent and constituting a primary fluid-receiving region of said bicomponent cover, and a nonperforated, nonwoven web secured to at least a portion of the outer periphery of said film, said nonwoven web being different from said thermoplastic film and constituting a secondary fluid-receiving region of said bicomponent cover; and d) separation means for controlling dispersion of body fluid downward, in the z-direction, away from said bicomponent cover and outward, in the x and y-directions, to enable said body fluid to contact a larger area of said absorbent, said separation means being positioned between only said thermoplastic film and said absorbent, and said first material in conjunction with said separation means has a rewet value of less than 0.1 grams.

46. An absorbent article comprising;

a) an absorbent;

b) a bicomponent cover at least partially enclosing said absorbent, said bicomponent cover including an apertured first material aligned along the longitudinal central axis of said absorbent and a nonapertured second material, said second material being different from said first material; and c) separation means for controlling dispersion of body fluid downward, in the z-direction, away from said bicomponent cover, said separation means being positioned between only said first material and said absorbent and being secured to said first material, and said first material in conjunction with said separation means has a rewet value of less than 0.1 grams.

47. An absorbent article comprising;

a) an absorbent;

b) a bicomponent cover at least partially enclosing said absorbent, said bicomponent cover including a net material having openings located between intersecting strands and which is aligned along the longitudinal central axis of said absorbent and a nonapertured second material secured to at least a portion of the outer periphery of said first material, said second material being different from said net material; and c) separation means for controlling dispersion of body fluid downward, in the z-direction, away from said bicomponent cover, said separation means being positioned between only said net material and said absorbent, and said first material in conjunction with said separation means has a rewet value of less than 0.1 grams.

48. An absorbent article comprising:

a) an absorbent having a first surface and a longitudinally extending central axis;

b) a bicomponent cover enclosing at least said first surface of said absorbent, said bicomponent cover including a first material having openings formed therethrough and a second material which is secured to said first material, said second material being different from said first material; and c) separation means for controlling dispersion of body fluid downward, in the z-direction, away from said bicomponent cover, said separation means being positioned between only said first material and said first surface of said absorbent and being aligned along said longitudinally extending central axis of said absorbent;

wherein said first material in conjunction with said separation means has a rewet value which is at least 10% lower than the rewet value of said second material without said separation means.

* * * * *